United States Patent [19]

Harman, III et al.

[11] Patent Number: 4,650,562

[45] Date of Patent: Mar. 17, 1987

[54] REFERENCE ELECTRODE DEVICE

[75] Inventors: John N. Harman, III, Placentia; R. Murty Neti, Brea, both of Calif.

[73] Assignee: Beckman Industrial Corporation, Cedar Grove, N.J.

[21] Appl. No.: 819,283

[22] Filed: Jan. 16, 1986

[51] Int. Cl.$^4$ ............................................. G01N 27/36
[52] U.S. Cl. ...................................... 204/420; 34/12; 204/433; 204/435; 324/438; 432/9
[58] Field of Search ............... 204/435, 420, 433, 1 H; 73/1 R; 324/438; 432/9; 34/12

[56] References Cited

U.S. PATENT DOCUMENTS 3,129,160  4/1964  Carter ................................. 204/420
3,306,837  2/1967  Riseman et al. ..................... 204/420

FOREIGN PATENT DOCUMENTS 2548518  5/1977  Fed. Rep. of Germany ...... 324/438
  31289  3/1976  Japan .................................. 204/433
 271717  7/1964  Netherlands ........................ 204/420

Primary Examiner—G. L. Kaplan
Attorney, Agent, or Firm—Daniel H. Bobis

[57] ABSTRACT

A normal pH sensitive glass electrode is deactivated by exposure to thermal treatments at relatively high temperatures of approximately 190° C. for predetermined periods of time until the nominal electrode sensitivity is reduced to very low levels such that the output potentials of such deactivated glass electrode approach the characteristics desired for a theoretically perfect reference electrode.

Additionally, a method of forming a deactivated pH glass electrode including the steps of exposing a normal pH or other ion sensitive glass electrode to high temperatures in the order of 190° C. or higher for predetermined periods of time is disclosed.

Additionally, there is disclosed an electrode measuring assembly for use in a potentiometric measuring system including, a vessel having a sample solution to be measured therein and a pH measuring electrode pair consisting of a normal pH sensitive glass electrode half cell and a deactivated pH glass electrode half cell disposed in spaced relation and immersed in the sample solution in said vessel, to be measured. The respective normal pH sensitive glass electrode half cell and the deactivated pH glass electrode are calibrated by suitable buffer solutions and a variable span analyzer before the electrode measuring assembly is connected into the potentiometric measuring system.

14 Claims, 2 Drawing Figures

REFERENCE ELECTRODE DEVICE

BACKGROUND OF THE INVENTION

The present invention relates generally to the measurement of a specific ion activity or concentration in solution by potentiometric measuring, recording and controlling systems in which the ion concentration is sensed by an electrode measuring assembly or reference cell which is electrically connected to a suitable measuring meter, and more particularly to the method for making and the embodiment of a deactivated pH or other ion sensitive glass electrode which when combined or paired as a half-cell with a normal pH or other ion sensitive glass electrode will provide an electrode measuring assembly or reference cell having the characteristics of a theoretically perfect reference electrode cell and therefore is adapted for use in such potentiometric measuring, recording and controlling systems for measuring pH or other ion concentrations in a given sample solution.

It is well known in the prior art that hydrogen ion concentration in a given sample solution can be measured with a pH measuring system. In todays conventional pH measuring systems used in industrial processes such as water conditioning and waste control, these systems include, an electrode measuring assembly or reference electrode cell to sense the pH which consists of a normal pH sensitive glass electrode half-cell coupled with a reference electrode half-cell of the flowing or non-flowing junction type and sometimes such units include a temperature sensor. The electrode measuring assembly is electrically connected either directly or through an amplifying arrangement to a pH meter having a suitable electromotive force thereacross and the pH meter reads out the measurements in millivolts. The readings which represent hydrogen ion activity in the solution being measured can be extrapolated to provide the hydrogen ion concentration.

These systems and the parts therefor are well known to those skilled in the art and the systems and their parts are available in the commercial marketplace from various manufacturers such as Beckman Industrial Corporation of Fullerton, Calif. and Cedar Grove, N.J. Therefor when the description set forth herein including the examples refer to a normal pH sensitive glass electrode, it is intended to mean electrodes of the type which are sold in the commercial marketplace by Beckman Industrial Corporation.

The normal pH sensitive glass electrode used in these systems is a generally elongated hollow, cylindrical glass member having the shape of a test tube which is closed at the immersion end and open at the opposite or remote end. The closed or immersion end of the pH glass electrode has a dome, bulb or other suitable configuration and extending through a suitable sealing means for the open end of the glass member and downwardly along the medial portion of the hollow inner chamber formed in the elongated glass member of the pH sensitive glass electrode is a suitable conductive wire element surrounded in assembled position by a buffered filling solution having a generally constant hydrogen ion and chloride ion concentration which is sealed in the inner chamber.

The glass wall of the elongated glass members of the pH sensitive glass electrode must meet many requirements. For example, it must during operation provide a span of nearly ideal millivolt readings for each given change in pH unit throughout the entire pH scale with little error in very acid or very alkaline solutions. Generally the composition of the glass membrane or wall of a pH sensitive glass electrode will consist of some combination of univalent, bivalent or trivalent metal or metals, and silicon dioxide mixed in varying ratios by weight to produce the desired compromise between response and resistance which is inherent for the thickness of each particular composition of glass used for the glass wall of the elongated glass member. In practice, manufacturers will produce several types of pH sensitive glass electrodes some with a narrow range, for example a pH range from 0 to 11 units; and others with a full pH range from 0 to 14 units.

In theory, it is believed that the ability of a particular pH sensitive glass electrode to respond to change in the hydrogen ion activity in a given solution is a function of the water content of the composition selected for the wall of the given glass member. The surface or more particularly the insertion tip end of the pH sensitive glass electrode swells slightly when immersed in a solution to be tested. In theory again it is beleived that a hydrated layer is formed as the water solution penetrates into the silicate network of the glass membrane or wall portion of the pH sensitive glass electrode immersed in the solution being tested and that this hydrated layer tends to facilitate migration of ions because it lowers the electrical resistivity of the glass wall; to the extent that an ion exchange equilibrium can be established across the phase-boundry between the hydrated layer and the glass wall; by the hydrogen ions in the solution being tested and the alkali metal ions in the glass wall of the normal pH sensitive glass electrode. This equilibrium is the potential established in the pH glass sensitive electrode which is measured and this potential varies in a known manner with the change in hydrogen ion activity, as distinguished from the concentration of the hydrogen ion in the solution being measured.

The reference electrode supplies a stable reference potential against which the measured potential developed across the glass wall of the pH sensitive glass electrode may be compared and effectively used for analytical purposes in various ways.

The reference electrodes constructed in accordance with known prior art concepts of fabrication and design suffer from significant limitations. Thus prior art reference electrodes which incorporate a flowing junction while exhibiting low junction potential must be continually replenished with internal electrolyte and unless counter pressurized are subject to intrusion from the solution or process fluid being measured. Non-flowing reference electrodes exhibit high junction potentials and are prone to junction plugging by deposits collected on the outer surface from the solution or process fluid being measured. Last, the electrolytic bridge present in both flowing and non-flowing reference electrodes is a necessary, but undesirable feature, since it enables cross diffusion of the solution or process fluid being measured and the internal electrolyte of the reference electrode which results in contamination of both the solution or process fluid and contamination of the internal electrolyte in the reference electrode half cell compartment.

The combination of the pH sensitive glass electrode half cell with the reference electrode half cell provides an electrode measuring assembly or cell to complete the measuring circuit read by the pH meter which is essentially a sensitive potentiometer acting in the circuit to balance off the differences in the respective potential in the pH sensitive glass electrode and the reference electrode. The pH meter reading will be either negative or positive depending upon the hydrogen ion activity in the solution being measured. It will provide a millivolt reading from which the equivalent hydrogen ion concentration for the solution can be extrapolated.

It has been found that when a normal unfilled or filled pH sensitive electrode is exposed to high temperature for a predetermined period of time; in either a dry temperature controlled environment such as an oven or in a wet temperature controlled environment such as in an immersion liquid in a pressurized autoclave, the nominal electrode senstivity of the normal pH sensitive electrode is reduced to very low levels and that the output potentials of such deactivated pH glass electrodes approach the characteristics desired for a theoretically perfect reference electrode.

Because of these unusual characteristics, a deactivated glass electrode can be combined or coupled with a conventional pH or ion sensitive glass electrode to provide an electrode measuring assembly or cell which when calibrated in suitable buffer solutions will be adapted for use in a potentiometric measuring system in place of the conventional known prior art electrode measuring assemblies with flowing or non flowing junction type reference electrode half cells such that (a) the respective glass membranes or walls prevent fluid transport between the electrodes for the respective half cells of the combination electrode assembly, (b) eliminate the requirement for refilling such as is needed for a flowing junction type of reference electrode, (c) prevents cross contamination because the electrodes in the respective half cells are separated by their glass membranes or walls, (d) insures that the respective temperature coefficients are at all times equal in the respective electrodes by the symmetry of the respective pH sensitive glass electrode and the deactivated pH glass electrode and the close proximity of the electrodes in the sample solution being measured, Further, it has been determined that deactivation or degradation of a pH or ion sensitive glass electrode is a function of the bulk property of the glass, not a surface phenomenon to the extent that erosion of the outer surface of the glass membrane or wall in the dome or bulb of the immersion end of the pH sensitive glass electrode due to etching or abrasion will not change the characteristics of the deactivated glass electrode insofar as its pH or ion response sensitivity is concerned.

Since the deactivation or degradation of a pH sensitive glass electrode is a function of the bulk property of the glass and not a surface phenomenon, it has been concluded that exposing the glass walls of the filled or unfilled pH sensitive glass electrode causes sufficient dehydration of the glass wall to deplete alkaline ions and the like pH sensitive sites on the outer surface and in the wall of the glass electrode. As a result, the normal pH sensitive glass electrode becomes a high-impedance structure which is difficult to rehydrate because of the missing alkaline ions. Such a deactivated pH or other ion sensitive glass electrode will be insensitive to changes in the pH or to other ion concentration in the solution being measured or monitored.

As another possibility, it has been hypothesized that when the conventional pH sensitive glass electrode is exposed to intense thermal conditions for a given period of time that the glass electrode is converted or forms hydrated silica sites or a silicon/dioxide/water mixture on the outer surface and in the wall defining the glass electrode.

SUMMARY AND OBJECTS OF THE INVENTION

Thus the present invention covers an improved half cell as a reference electrode for use in potentiometric measurement systems comprising, a glass electrode including, a. an elongated glass member having a composition sensitive to a given ion activity in a solution, b. said glass member at the immersion end having a predetermined wall thickness, and said wall made from monovalent, bivalent and trivalent alkaline metals and silicon dioxide, and c. said elongated glass member having at least the immersion end thereof deactivated by exposure for predetermined periods of time to high temperatures, to decrease the ion sensitivity of the glass electrode to relatively low levels.

Additionally, the combination of the above described deactivated ion sensitive glass electrode half cell with a normal pH or other ion sensitive glass electrode to provide an electrode measuring assembly or cell for use in a potentiometric ion measurement system.

Additionally, the method of deactivating a normal pH or other ion sensitive glass electrode by the steps of exposing the pH or ion sensitive glass electrode for predetermined periods of time at ambient atmospheric pressure to high temperature until the output potential thereof is degraded to reduce the sensitivity of this normal glass pH or other ion sensitive glass electrode to one which approximates the characteristics desired in a theoretically perfect reference electrode.

Additionally, the method of deactivating a pH or ion sensitive glass electrode as above described in which the thermal deactivation is accomplished by exposing the normally pH or ion sensitive glass electrode to temperatures of about 190° C. or higher for predetermined periods of time as a function of the temperature.

Accordingly, it is an object of the present invention to provide an ion sensitive glass electrode deactivated by exposure to high temperatures for predetermined periods of time so as to operate as a theoretically perfect reference electrode.

It is another object of the present invention to provide an electrode measuring assembly for use in a potentiometric pH measuring system which includes a normal pH sensitive glass electrode and a deactivated pH sensitive glass electrode adapted to operate with the characteristic of a theoretically perfect reference electrode.

It is another object of the present invention to provide an electrode measuring assembly for use in a pH measuring system which eliminates the junction potentials common to conventional prior art electrode measuring cells having reference electrodes incorporating a flowing junction.

It is another object of the present invention to provide an electrode measuring assembly for use in a pH measuring system which eliminates cross diffusion between the sample and the electrolyte in the conventional prior art reference electrode half cell incorporating a flowing junction.

It is another object of the present invention to provide an electrode measuring assembly for use in a pH measuring system which eliminates junction plugging common to conventional prior art electrode measuring cells having reference electrodes of the non-flowing junction type.

It is another object of the present invention to provide an electrode measuring assembly for use in a pH measuring system in which the respective half cells are symmetrical in structure and are so disposed in the solution that the temperature coefficient for the respective electrodes in each half cell will be equal to each other.

It is a further object of the present invention to provide a deactivated ion sensitive glass electrode adapted to operate as a theoretically perfect reference electrode which is insensitive to the change in ion concentration of the sample solution being measured.

It is a still further object of the present invention to provide a deactivated ion sensitive glass electrode adapted to operate as a theoretically perfect reference electrode in which the erosion on the outer surface of the immersion end of the glass electrode by abrasion or etching will not change the ion responsive properties of the deactivated glass electrode.

With these and other objects in view the invention will be better understood from the description and Claims which follow hereinafter taken with reference to the drawings in which:

Figure 1:
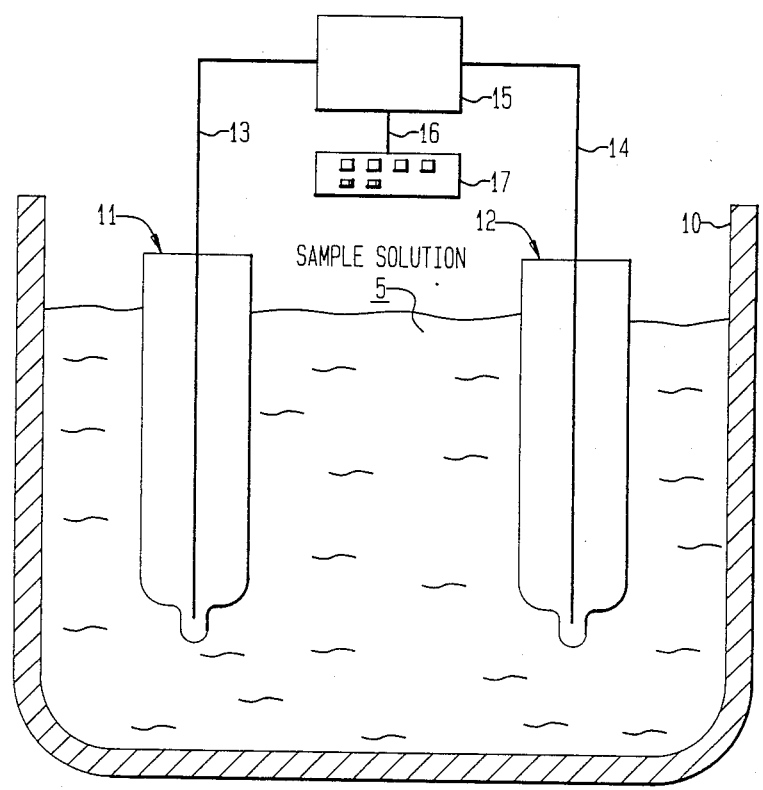
FIG. 1 is a diagramatic sketch of a simplified form of potentiometric measuring system including an electrode measuring assembly having a normally pH sensitive glass electrode, a deactivated pH glass electrode in accordance with the present invention, and a pH meter.

DESCRIPTION OF A PREFERRED METHOD AND EMBODIMENT FOR A REFERENCE ELECTRODE DEVICE

Those skilled in the art know that the electrode potential or output signal of a normal pH sensitive glass electrode has a pH sensitivity span of approximately 60 millivolts (mV) per decade of pH unit change at normal room temperature (approximately 25° C.).

This is noted because the method of the present invention is capable of inducing a decrease or degradation in the pH sensitivity of such pH sensitive glass electrode from this theoretical span value to a span value of less than 10 mV per decade to thus obtain the advantage that when such deactivated or degraded pH glass electrode is used as a reference electrode half cell with a normal pH sensitive glass electrode half cell in an electrode measuring assembly or reference cell for use in a potentiometric measuring system the electrode measuring assembly or reference cell can approach the characteristics desired for a theoretically perfect reference cell in that in such improved electrode measuring assembly or reference cell there is no direct contact of two electrolytic solution phases which create a junction potential as in existing prior art devices; the glass walls or membranes of the respective glass electrodes of the two half cells provide a barrier which prevents fluid transport across either of the units in the cell, eliminates the requirement for replacing electrolytic fluid as is required in flowing junction type reference cells, and eliminates the problem of cross-contamination which will occur in flowing junction type reference half cells.

The method of the present invention induces the desired property for such improved reference electrode by the thermal treatment of either an unfilled or filled normally pH sensitive glass electrode in either the dry temperature controlled environment of an oven or in the wet temperature controlled environment provided by immersion or subjection to a liquid in a pressurized autoclave. Both of these methods reduce the nominal pH electrode sensitivity span to levels useful for it to function as a reference electrode which approaches the properties for a theoretically perfect electrode as above set forth.

The following examples illustrate the application of the method in accordance with the present invention to provide a deactivated normal pH sensitive glass electrode which will operate as a reference electrode half cell in an electrode measuring assembly or reference cell for use in a potentiometric pH measuring system.

EXAMPLE NO. 1

A normal pH sensitive glass electrode was placed in an oven at ambient, atmosphere, temperature, and pressure, and the temperature of the oven was raised and maintained at 150° to 170° C. for a period of fourteen (14) hours.

This thermally treated normal pH sensitive glass electrode was removed from the oven and allowed to cool, then it was tested and it was determined that only insignificant deactivation of pH sensitivity of the normal pH sensitive glass electrode had been effected.

EXAMPLE NO. 2

A normal filled pH sensitive glass electrode was placed in an oven at ambient, atmosphere, temperature and pressure, and the temperature of the oven was raised and maintained at 190° C. for a period of twelve (12) hours.

This normal pH sensitive glass electrode was removed from the oven and allowed to cool, then it was tested. No open circuit like behavior was noted and on visual examination no cracks were found in the glass wall of the glass electrode. Test measurements showed that the thermal treatment had induced a decrease of the pH sensitive span for this normal pH sensitive glass electrode to less than 10 mV per decade for each unit change of pH of a measured sample solution at 25° C.

This deactivated pH glass electrode was calibrated with suitable buffer solutions and a variable span analyzer and when coupled with a normal pH sensitive glass electrode to provide a pair of coacting half cells for an electrode measuring assembly or reference cell was found to operate and function well in a potentiometric measuring system used to measure induced changes in the pH in a suitable sample solution used for testing this reference cell.

EXAMPLE NO. 3

A normal pH sensitive glass electrode was placed in an oven at ambient, atmosphere, temperature, and pressure and the temperature of the oven was raised and maintained at 200° C. for a period of forty-eight (48) hours.

This normal pH sensitive glass electrode was removed from the oven, cooled and tested. No open circuit like behavior was noted and on visual examination no cracks were found in the glass wall of the glass electrode. The test showed that the electrical impedance of this deactivated pH sensitive glass electrode had increased at least by a factor of $10^3$. Test measurements of temperature treated normal pH sensitive glass electrode showed a substantial decrease of the pH sensitive span thereof in the same order as that achieved in Example No. 2. This deactivated pH glass electrode was then calibrated with suitable buffer solutions and a variable span analyzer and coupled with a normal pH sensitive glass electrode to provide a pair of coacting half cells for an electrode measuring assembly or reference cell. This last mentioned electrode measuring assembly or reference cell when operated was found to function well in a potentiometric measuring system used to measure induced changes in the pH in a suitable sample solution used for testing this electrode measuring assembly or reference cell.

EXAMPLE NO. 4

A normal filled pH sensitive glass electrode was immersed in distilled water in an autoclave and subjected to temperatures of 200° to 250° C. at system pressures of 1000 PSIG for a period of fourteen (14) hours.

Thereafter this thermally treated normal filled pH sensitive glass electrode was removed from the autoclave, cooled, visually inspected and tested and found to have no open circuit behavior or cracks in the glass wall of the glass electrode. The test further showed that the electrical impedance level of this normal filled pH sensitive glass electrode had increased to a level in a range from $10^3$ to $10^5$.

The test also showed that despite the increased impedance this normally filled pH sensitive glass electrode had been sufficiently deactivated or degraded that the pH sensitivity levels were reduced sufficiently to make it useful as a reference electrode half cell with a normal pH sensitive glass electrode half cell in an electrode measuring assembly for a potentiometric system measuring induced changes in pH in a suitable sample station used for testing this electrode measuring assembly or reference cell.

EXAMPLE NO. 5

A normal filled pH sensitive glass electrode was immersed in a buffer solution at pH 4 and subjected to the same conditions set forth for the normal filled pH sensitive glass electrode as set forth in Example No. 4 above.

The results observed when the temperature and pressure treated normal filled pH sensitive glass electrode was removed from the autoclave were the same as those set forth for Examples No. 3 and 4 above.

EXAMPLE NO. 6

A normal filled pH sensitive glass electrode was immersed in a buffer solution of pH 7, placed in an autoclave and subjected to the same conditions of temperature and pressure as set forth in Examples No. 3 and 4 above.

The results observed when the temperature and pressure treated normal filled pH sensitive glass electrode was removed from the autoclave were the same as those set forth for Examples No. 3 and 4 above.

EXAMPLE NO. 7

A normal filled pH sensitive glass electrode was immersed in a buffer solution at pH 10, placed in an autoclave and subjected to the same temperature and pressure conditions set forth in Examples No. 3 and 4 above.

The results observed when the temperature and pressure treated normal filled pH sensitive glass electrode was removed from the autoclave were the same as those set forth for Examples No. 3 and 4 above.

All of the above enumerated Test Examples were also conducted for normal, unfilled, pH sensitive glass electrodes and substantially identical test results were achieved.

The above examples demonstrate that a normal filled or unfilled pH sensitive glass electrode can be subjected to temperature treatment over a period of time and as long as the thermal deactivation treatment was above a minimum threshold temperature it will induce a reduction more or less in pH sensitivity so that the deactivated or degraded pH glass electrode produced, functioned as a half cell with a normal pH sensitive glass electrode, to provide an electrode measuring assembly or reference cell for use in a potentiometeric measuring system.

The above examples are merely illustrative of the method and embodiment of the reference electrode device in accordance with the present invention. However, it is difficult to fully define the time and temperature parameters that will serve to map the entire range of dry and wet treatment conditions which will induce the desired deactivated pH or other ion sensitive glass electrode for the purpose and objects set forth herein.

The specific procedure required in accordance with the method of the present invention for a particular application or use has been found to be a function of the electronic design characteristics of the amplifier and the other elements of the potentiometric measuring equipment and will depend on how much differential response (span mV/per decade) for each pH unit change will be needed for a given application to provide a meaningful measurement.

It is possible for example to design a functional pH measurement system which needs only a span of 1 to 5 mV/decade of pH change for the electrode measuring assembly or reference cell consisting of a normal pH sensitive glass electrode/deactivated pH glass electrode in accordance with the present invention. This would mean that the thermal treatment process in accordance with the present invention would only be required to degrade or deactivate the response of the thermally treated pH sensitive glass electrode by from 1 to 5 mV/decade or to a pH response having a span of 58 to 54 mV/decade as distinguished from the nominal mV/decade of hydrogen ion activity or concentration change of ~60 mV/decade applicable to a normal pH sensitive glass electrode.

The examples set forth above show that in accordance with the present invention that the pH sensitivity level of a normal pH sensitive glass electrode can be reduced to levels as low as or lower than 10 mV/decade level.

Thus, it is possible with the present invention to achieve thermal treatment cycles at lower temperatures and shorter times if it is not necessary to meet the low span sensitivity reduction levels which can be achieved in accordance with the present invention.

Now referring to FIG. 1 a potentiometric measuring system is diagrammatically illustrated for measuring pH ion concentrates which includes an electrode measuring assembly or reference cell generally designated 10 having a normally pH sensitive glass electrode half cell 11 and a deactivated pH glass electrode half cell 12 in accordance with the present invention which serves as the reference electrode when formed into the electrode measuring assembly 10. The electrodes 11 and 12 are connected as by lines 13 and 14 to an electrical signal amplifier 15 which acts to amplify the electrical signals transmitted from the respective normal pH sensitive glass electrode half cell 11 and the deactivated reference cell 12. Amplifier 15 transmits the signals via line 16 to a potentiometric measuring and extrapolating instrument 17 which has a suitable meter for reading the millivolt changes of the sample solution S in the electrode measuring assembly or reference cell 10. This system differs from the conventional prior art systems only to the extent that the reference electrode half cell consists of a deactivated normal pH sensitive glass electrode in accordance with the present invention.

The operation of this system is identical with the conventional and well known systems presently in use in the prior art having reference electrode half cells of the flowing or non-flowing junction type and therefore those skilled in the art will readily understand how the diagramatically illustrated system as shown in FIG. 1 operates.

In this system as shown in FIG. 1 the respective normal or commercial pH sensitive glass electrode 11 and the deactivated pH glass electrode 12 will be calibrated with suitable buffer solutions and a variable span analyzer in accordance with the methods known in the prior art for calibrating these measuring cells before the cell is placed into actual use in a potentiometric measuring system.

Since the normal or commercial pH sensitive glass electrode and the deactivated pH glass electrode operating as a reference electrode are disposed in the same sample solution which is being monitored and they are in relatively close proximity, the respective temperature coefficients in each of the respective electrodes will be equal and therefore the necessity for a suitable mechanism for adjusting for temperature changes which is normally required in the prior art systems is eliminated.

Since the deactivated pH glass electrode operating as a reference electrode in the electrode measuring assembly 10 will be substantially insensitive to changes in the hydrogen ion activity of the sample solution, the electrode potential of the reference electrode half cell 12 will be substantially invariant and independent of pH. Thus, as the potential of the normally pH sensitive glass electrode half cell in the electrode measuring assembly or reference cell 10 changes, this potential can be compared against the potential of the deactivated pH glass electrode half cell to provide a pH measurement which is equivalent to the hydrogen ion activity in the sample solution being monitored. This pH activity signal can be extrapolated by the potentiometric measuring equipment to provide the hydrogen ion concentration in the solution by the conventional means well known in this art.

Figure 2:
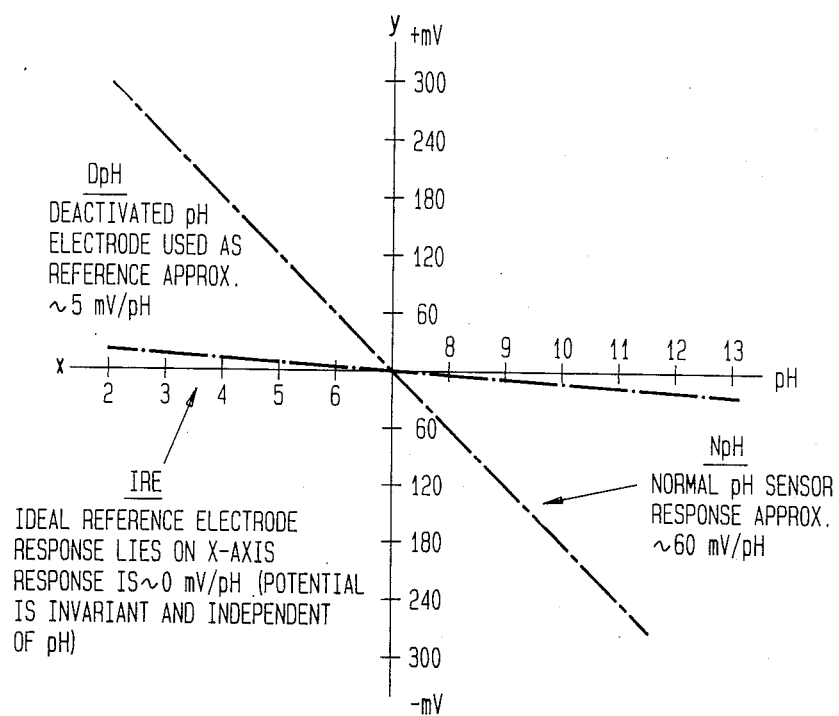
FIG. 2 is a graphical representation of the potential of a normally pH sensitive glass electrode, a deactivated pH sensitive glass electrode, and a theoretically perfect or ideal reference electrode.

FIG. 2 is a graphical representation for a pH measuring system in which the X or horizontal axis is divided into equivalent pH units and the Y or vertical axis which bisects the X axis at pH 7 shows positive millivolts above the X axis and negative millivolts below the X axis. The measurements shown thereon were taken at ambient room temperature of approximately 25° C.

By reference to FIG. 2 the electrode response for an ideal or perfect reference electrode is coincident with or lies along the X axis and is designated with the legend IRE. This shows that the ideal reference electrode IRE has an electrode potential or signal response which is invariant and independent of the pH of the sample solution being monitored and is represented by the equation $\sim 0$ mV/pH.

The electrical response for normal or commercially utilized pH sensitive glass electrode half cells is shown by the dashed line designated NpH and this line shows that the electrode potential sensed by such normal pH sensitive glass electrode half cell has a span of approximately 60 millivolt per decade change in pH units at room temperature (approximately 25° C.) which is represented by the equation $\sim 60$ mV/pH.

The electrical response of a deactivated pH glass electrode is shown on the graph by the dot dash line DpH which indicates that the deactivated pH glass electrode deviates from the electrical response of an ideal reference electrode by approximately 5 millivolts per unit or decade of pH which is represented by the equation $\sim 5$ mV/pH.

As long as the ratio of the slope of the lines for a normal or commercial pH sensitive glass electrode half cell and a deactivated pH glass electrode used as a reference electrode half cell in an electrode measuring assembly or reference cell are reasonably constant, the respective electrode half cells making up the electrode measuring assembly may be calibrated in conventional fashion with buffer solutions and a variable span analyzer and will operate to provide an electrode measuring assembly for use in a potentiometric measuring system for measuring pH changes in a solution to be monitored.

While it has not been clearly demonstrated by examples such as those provided for a normal pH sensitive glass electrode, it is inherent in the present disclosure that the reference cells established in accordance with the present invention will be equally applicable to the deactivation of other ion sensitive glass electrodes to provide reference electrode half cells to be used therewith for forming electrode measuring assemblies or reference cells for use in potentiometric measuring systems for measuring changes in that particular ion in a solution being monitored.

Thus, an improved reference electrode device has been shown and described above which will provide a substantially accurate measurement of the pH or other ion activity or concentration for a given sample solution.

It will be understood that the invention is not to be limited to the specific construction or arrangement of parts shown but that they may be widely modified within the invention defined by the claims.

What is claimed is:

1. A deactivated glass electrode half cell, for use in a potentiometric measuring system for measuring and monitoring specific ion activity in a sample solution, made by heat treating a glass electrode normally sensitive to the specific ion, comprising
   a. a glass vessel,
   b. said glass vessel having a wall composed of monovalent, bivalent and trivalent metals and silicon dioxide,
   c. said glass vessel deactivated at temperatures of at least 150° C. for periods of time of at least 12 hours to induce a decrease in span sensitivity to the specific ion, and d. said deactivated glass electrode operable to provide signal potentials to the potentiometric measuring system substantially equivalent to a theoretically ideal reference electrode glass cell.

2. The half cell as claimed in claim 1 wherein the normal ion sensitive glass electrode is a normal pH sensitive glass electrode having a span sensitivity of about 60 mV/decade of pH change.

3. The half cell as claimed in claim 2 wherein the deactivation by thermal exposure reduces the span sensitivity of the tubular glass vessel of the normal pH sensitive glass electrode to as low as 10 mV/decade of pH change.

4. The half cell as claimed in claim 2 wherein the deactivation by thermal exposure is done at said temperatures for periods of time in a range from 12 hours to 48 hours.

5. The half cell as claimed in claim 2 wherein the deactivation by thermal exposure increases the electrical impedance of the deactivated glass electrode to $10^5$.

6. In a reference cell for use in potentiometric measuring systems for measuring and monitoring pH activity in a sample solution including, a. vessel means for receiving the sample solution to be measured and monitored, b. a normal pH sensitive glass electrode half cell disposed in said vessel means for immersion in the solution therein, c. a deactivated glass electrode half cell disposed in said vessel means a spaced distance from said normal pH sensitive glass electrode half cell and also immersed in the said sample solution, d. a potentiometric measuring system including, a pH meter for receiving the electrical signal potential of the respective normal pH sensitive glass electrode and the deactivated glass electrode to measure changes in pH activity and concentration in the sample solution, and e. said deactivated glass electrode deactivated by exposure to temperatures of at least 150° C. for periods of time of at least 12 hours to induce a decrease in the span sensitivity to the pH ion as a function of the electrical characteristic and measurement requirements of the associated potentiometric measuring system, f. said deactivated glass electrode operable to provide signal potential to the potentiometric measuring system substantially equivalent to a theoretically ideal reference electrode half cell.

7. A reference cell as claimed in claim 6 wherein the deactivation by thermal exposure reduces the span sensitivity of the deactivated glass electrode to as low as 10 mV/decade of pH change.

8. The reference cell as claimed in claim 6 wherein the deactivation by thermal exposure of the deactivated glass electrode is done at said temperatures for periods of time in a range from 12 hours to 48 hours.

9. The method of forming a deactivated glass electrode for use as a reference electrode half cell in a reference cell for use in a potentiometric measuring system for measuring a given ion in a sample solution including the steps of:

a. placing a normal ion sensitive glass electrode at ambient atmosphere and pressure in a thermal treating device, b. raising the temperature of the thermal treating device to at least 150° C., c. maintaining the normal ion sensitive glass electrode in the thermal treating device at these elevated temperature conditions for periods of time in a range from 12 hours to 48 hours, and d. removing the deactivated ion sensitive glass electrode from the thermal treating device and cooling the same, and e. calibrating the deactivated ion sensitive glass electrode by suitable use of buffer solution and a variable span analyzer before the use thereof as a reference cell.

10. The method of forming a deactivated glass electrode half cell as claimed in claim 9 wherein the normal ion sensitive glass electrode is a normal pH sensitive glass electrode having a span sensitivity of about 60 mV/decade of pH change.

11. The method of forming a deactivated glass electrode as claimed in claim 9 including the step of maintaining the thermal exposure until the span sensitivity of the normal pH sensitive glass electrode is reduced to at least 10 mV/decade of pH change.

12. The method of forming a deactivated glass electrode as claimed in claim 9 including the steps of maintaining the normal pH sensitive glass electrode at the temperature conditions in the thermal treating device for periods of time sufficient to induce the deactivated glass electrode to provide signal potentials to the potentiometric measuring system substantially equivalent to a theoretically ideal reference electrode.

13. The method of forming a deactivated glass electrode as claimed in claim 9 wherein the thermal treating device is in the form of a dry oven.

14. The method of forming a deactivated glass electrode as claimed in claim 9 wherein the thermal treating device includes an autoclave having a source of water therein.

* * * * *